United States Patent
Davis et al.

(10) Patent No.: US 8,235,940 B2
(45) Date of Patent: Aug. 7, 2012

(54) TROCAR ENTRY INCORPORATING AN AIRBAG

(75) Inventors: Michael Davis, Middletown, CT (US);
Stanislaw Marczyk, Stratford, CT (US);
Peter Hathaway, Lebanon, CT (US);
Brian Creston, West Haven, CT (US);
Gregory G. Okoniewski, North Haven, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/224,361

(22) Filed: Sep. 2, 2011

(65) Prior Publication Data
US 2011/0319819 A1     Dec. 29, 2011

Related U.S. Application Data

(63) Continuation of application No. 12/620,829, filed on Nov. 18, 2009, now Pat. No. 8,048,027.

(60) Provisional application No. 61/121,653, filed on Dec. 11, 2008.

(51) Int. Cl.
*A61M 29/00* (2006.01)
*A61M 5/00* (2006.01)

(52) U.S. Cl. ........ 604/99.01; 604/96.01; 604/117; 604/103.03; 604/264; 606/185

(58) Field of Classification Search ........ 606/185, 606/191, 205, 41–46; 424/422–425, 438; 600/104–108, 114, 204, 208, 463, 564–568; 604/117, 164.01–164.12, 167.01–167.06, 604/174, 175, 180, 26, 264, 506
See application file for complete search history.

(56) References Cited

U.S. PATENT DOCUMENTS

| | | | |
|---|---|---|---|
| 4,738,666 A * | 4/1988 | Fuqua | 604/514 |
| 5,423,770 A * | 6/1995 | Yoon | 604/506 |
| 5,891,089 A | 4/1999 | Katz et al. | |
| 5,919,163 A * | 7/1999 | Glickman | 604/101.05 |
| 7,744,559 B2 | 6/2010 | Krishna | |
| 2002/0042594 A1 | 4/2002 | Lum et al. | |
| 2003/0181939 A1 | 9/2003 | Bonutti | |
| 2003/0204138 A1 | 10/2003 | Choi | |
| 2004/0102733 A1 * | 5/2004 | Naimark et al. | 604/65 |
| 2006/0058775 A1 | 3/2006 | Stevens et al. | |
| 2006/0064059 A1 * | 3/2006 | Gelfand et al. | 604/103.06 |
| 2006/0142827 A1 * | 6/2006 | Willard et al. | 607/105 |

FOREIGN PATENT DOCUMENTS
WO   WO 03/045290 A1   6/2003

OTHER PUBLICATIONS

European Search Report for EP 09252751.4-2310 date of completion is Mar. 1, 2010 (3 pages).

* cited by examiner

*Primary Examiner* — Nicholas Lucchesi
*Assistant Examiner* — Leah Stohr

(57) ABSTRACT

A safety trocar assembly incorporating an airbag is provided to prevent overpenetration of the safety trocar assembly through an abdominal wall and into a body cavity. The safety trocar assembly includes an airbag cannula having an expandable airbag proximal of the distal end of the cannula. A sensing device is located at a distal end of the cannula for detecting changes in conditions at the distal end of the cannula. A trigger mechanism is provided on the cannula and operates to inflate the airbag in response to a change in condition detected by the sensing device.

20 Claims, 12 Drawing Sheets

US 8,235,940 B2

TROCAR ENTRY INCORPORATING AN AIRBAG

CROSS-REFERENCE TO RELATED APPLICATION

This application is a continuation of U.S. patent application Ser. No. 12/620,829, filed on Nov. 18, 2009 now U.S. Pat. No. 8,048,027, which claims priority to, and the benefit of, U.S. Provisional Patent Application Ser. No. 61/121,653, filed on Dec. 11, 2008. The disclosures of these prior applications are hereby incorporated herein by reference in their entirety.

BACKGROUND

1. Technical Field

The present disclosure relates to a safety trocar assembly incorporating a structure to prevent overpenetration of the safety trocar assembly into an abdominal cavity. More particularly, the present disclosure relates to a safety trocar assembly incorporating an airbag and sensors associated with a distal end of the safety trocar assembly for detecting changes in conditions at the distal end of the safety trocar assembly.

2. Background of Related Art

During minimally invasive surgical procedures access ports or trocar assemblies are provided to penetrate an abdominal wall and provide a sealed pathway for insertion of surgical instruments into an abdominal cavity. These trocar assemblies typically include an access port or cannula having a housing and an elongate tubular member extending distally from the housing. A channel or lumen extends through the housing and elongate tubular member for receipt of surgical instruments. One or more valves or seals may be provided within the housing to seal against the surgical instruments. The trocar assemblies additionally include a tissue penetrating or incising device or obturator which is positioned through the cannula. The obturator typically includes a tissue penetrating tip at a distal end which, when assembled with the cannula, extends beyond the distal end of the cannula. Advancement of a trocar assembly against an abdominal wall causes the tissue penetrating tip of the obturator to penetrate the abdominal wall and allow passage of the distal end of the cannula into the abdominal cavity.

During insertion of the trocar assembly through the abdominal wall, care must be taken not to damage underlying organs by engagement with the tissue penetrating tip of the obturator or the distal end of the cannula. Various types of safety devices have been developed to shield underlying organs from the tissue penetrating tip of the obturator. In one type of safety trocar assembly, the obturator is maintained in a distal position relative to the cannula during insertion and is spring biased proximally such that upon penetration into the abdominal cavity the tissue penetrating tip of the obturator retracts within the distal end of the cannula. This shields underlying organs from the tissue penetrating tip of the obturator. In another type of safety trocar assembly, a spring biased outer sheath or shield is associated with the cannula such that, upon penetration of the abdominal wall by the tissue penetrating tip of the obturator, the outer sheath or shield advances distally to cover the tissue penetrating tip of the obturator again preventing damage to underlying organs.

While the known type of safety trocar assemblies incorporate methods of shielding underlying organs from the tissue penetrating tip of the obturator, these safety devices do not prevent continued advancement of the trocar assembly through the abdominal wall towards the underlying organs.

Therefore, a need exists for a safety trocar assembly which incorporates an expandable member located proximally of the distal end of the safety trocar assembly to prevent overpenetration of the safety trocar assembly through the abdominal wall. Further, a need exists for a safety trocar assembly having a sensor adjacent the distal end of the safety trocar assembly to detect changes in conditions at the distal end of the safety trocar assembly as it passes through the abdominal wall and into the body cavity.

SUMMARY

There is disclosed a safety trocar assembly including an airbag cannula and an obturator. The airbag cannula generally includes a housing and an elongate tubular member extending distally from the housing. An expandable member is positioned on the elongate tubular member proximal of a distal end of the elongate tubular member and is movable from a collapsed position to an expanded position. A sensor is provided including a sensor lumen formed through the elongate tubular member and having a sensor opening adjacent to the distal end of the elongate tubular member. A trigger mechanism is operatively associated with the sensor and the expandable member such that a change of condition sensed at the sensor opening operates to move the expandable member from the collapsed to the expanded position.

In one embodiment, the expandable member is an airbag positioned on the elongate tubular member. The elongate tubular member includes an inflation lumen in fluid communication with the airbag. The trigger mechanism includes a valve to inflate the airbag in response to a change in conditions detected by the sensor. A source of fluid pressure is operatively associated with the valve.

In one embodiment, the sensor is an air pressure sensor capable of detecting changes in air pressure at the sensor opening.

In an alternative embodiment, the sensor is an optical sensor including an optical fiber extending through the sensor lumen and terminating adjacent the sensor opening.

In a further alternative embodiment, the sensor is an ultrasound sensor.

In another embodiment, the sensor is a sonar sensor.

In a particular embodiment, a distal end of the airbag is longitudinally movable along and outer surface of the elongate tubular member.

In a further particular embodiment, the airbag includes a plurality of circumferentially spaced airbags.

In a specific embodiment, the airbag cannula includes an outer sheath overlying the airbag to restrain the airbag in the collapsed position. The outer sheath includes a perforation line which is separable upon inflation of the airbag from the collapsed to the expanded position.

There is also disclosed an airbag cannula having a housing and an elongate tubular member extending distally from the housing. An expandable member is positioned on the elongate tubular member proximal of a distal end of the elongate tubular member. The expandable member is movable from a collapsed position to an expanded position. A sensor is provided including a pair of sensor wires extending through the elongate tubular member and terminating in a pair of spaced apart sensor tips adjacent to the distal end of the elongate tubular member. A trigger mechanism is operatively associated with the sensor and the expandable member such that a change of condition sensed between the sensor tips operates to move the expandable member from the collapsed to the expanded position.

The sensor is an electrical sensor and the change in condition sensed between the sensor tips is a change in electrical resistance existing between the sensor tips.

The expandable member is an airbag positioned on the elongate tubular member. The elongate tubular member includes an inflation lumen in fluid communication with the airbag and the trigger mechanism includes a valve to inflate the airbag in response to a change in conditions detected by the sensor.

In one embodiment, a distal end of the airbag is longitudinally movable along and outer surface of the elongate tubular member.

In a further embodiment, the airbag includes a plurality of circumferentially spaced airbags.

The airbag cannula further includes an outer sheath overlying the airbag to restrain the airbag in the collapsed position. The outer sheath includes a perforation line which is separable upon inflation of the airbag from the collapsed to the expanded position.

There is also disclosed a method of preventing overpenetration of the distal end of a cannula into an abdominal cavity. The method includes providing a cannula having a housing and an elongate tubular member extending distally from the housing. An airbag is positioned on the elongate tubular member and the elongate tubular member includes an inflation lumen in fluid communication with the airbag. The airbag is positioned on the elongate tubular member proximal of a distal end of the elongate tubular member and is movable from a collapsed position to an expanded position. A sensor is provided including a sensor lumen formed through the elongate tubular member and having a sensor opening adjacent to the distal end of the elongate tubular member. A trigger mechanism is operatively associated with the sensor and the airbag, the trigger mechanism including a valve to inflate the airbag in response to a change in conditions detected by the sensor such that a change of condition sensed at the sensor opening operates to move the airbag from the collapsed to the expanded position.

The method includes the steps of positioning the distal end of the elongate tubular member adjacent an abdominal wall, such that the sensor opening is sealed against the abdominal wall, and sensing a first condition at the sensor opening.

The distal end of the elongate tubular member is advanced through the abdominal wall and into an abdominal cavity. A second condition is sensed at the sensor opening and the airbag is inflated from the collapsed position to the expanded position in response to a change in condition between the first condition and the second condition sensed at the sensor opening.

DESCRIPTION OF THE DRAWINGS

Various embodiments of the presently disclosed safety trocar assembly are disclosed herein with reference to the drawings, wherein.

DETAILED DESCRIPTION OF EMBODIMENTS

Embodiments of the presently disclosed safety trocar assembly with airbag cannula will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
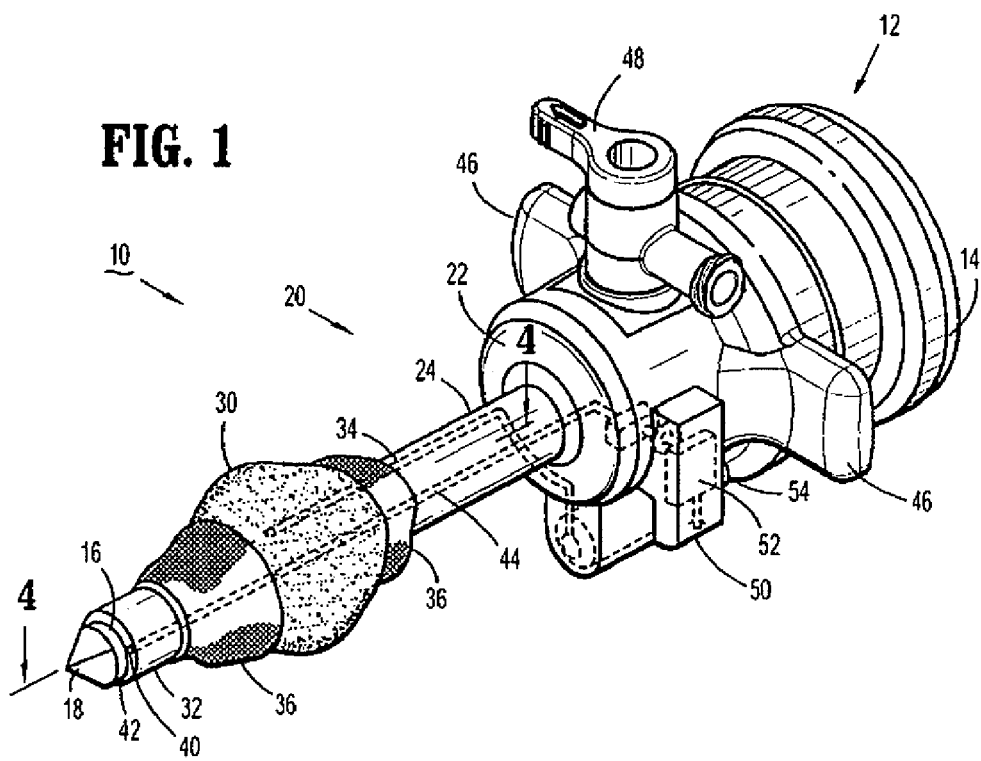
FIG. 1 is a perspective view of one embodiment of a safety trocar assembly including an obturator and an airbag cannula incorporating one embodiment of an airbag.
Figure 2:
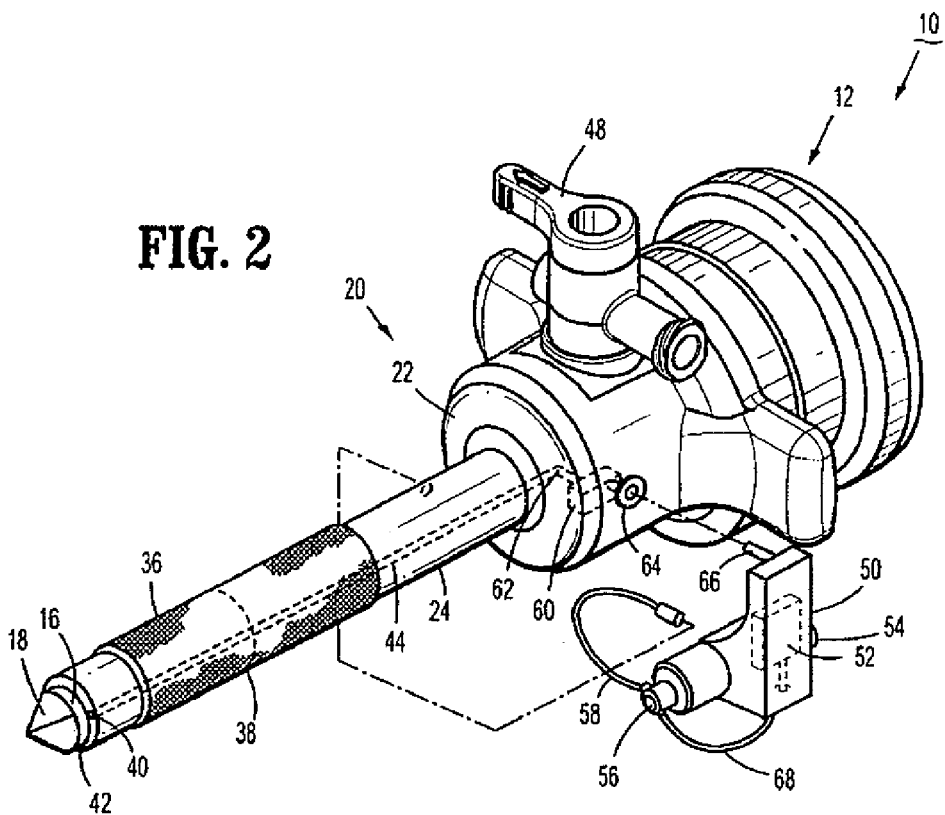
FIG. 2 is a perspective view of the safety trocar assembly of FIG. 1 with a triggering mechanism removed.
Figure 3:
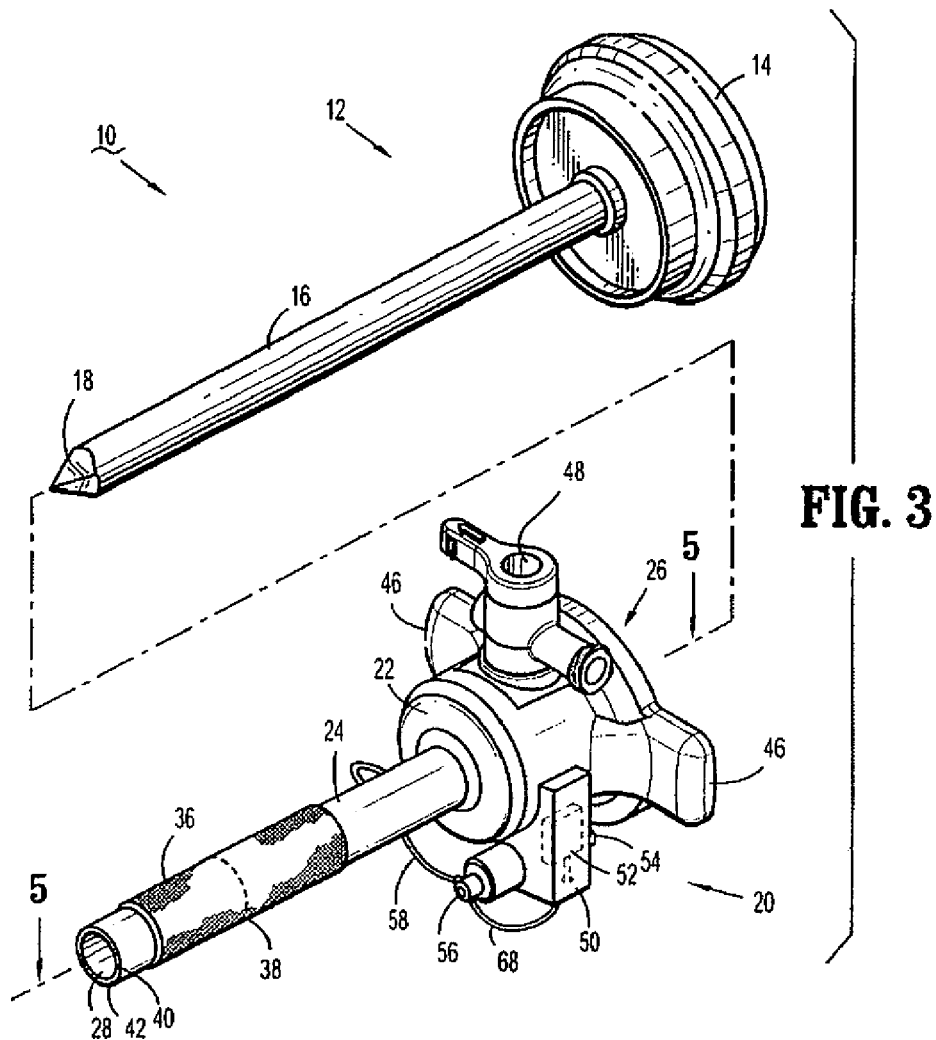
FIG. 3 is a perspective view of the safety trocar assembly of FIG. 1 with the obturator of the safety trocar separated from the airbag cannula of the airbag trocar.

Referring initially to FIGS. 1-3, there is disclosed a safety trocar assembly 10 for use in surgical procedures. Safety trocar assembly 10 is designed to prevent overpenetration through the abdominal wall and thus prevent damage to underlying organs. Safety trocar assembly 10 includes an obturator 12 having a handle 14 and an elongate shaft 16 extending distally from handle 14. Elongate shaft 16 terminates in a tissue penetrating tip 18 which is provided to puncture through an abdominal wall. Safety trocar assembly 10 further includes an airbag cannula 20 configured to receive obturator 12 therethrough. Airbag cannula 20 generally includes a housing 22 having a hollow, elongate tubular member 24 extending distally from housing 22. A throughbore 26 extends through housing 22 and is in communication with a lumen 28 extending through elongate tubular member 24. In the assembled condition, obturator 12 extends through throughbore 26 and lumen 28 of airbag cannula 20.

Referring for the moment to FIG. 1, airbag cannula 20 includes an expandable member in the form of a balloon or airbag 30 positioned on an outer surface 32 of elongate tubular member 24. Airbag 30 is formed of a flexible, non-expansible material. An inflation lumen 34 extends through elongate tubular member 24 and is in fluid communication with airbag 30. Upon penetration of an abdominal wall, an inflation fluid is forced through inflation lumen 34 and into airbag 30 to move airbag 30 from a deflated to an inflated condition as described in more detail hereinbelow.

Referring back to FIGS. 1-3, an outer sheath 36 is provided to restrain airbag 30 in the deflated condition. Outer sheath 36 is affixed to outer surface 32 of elongate tubular member 24. A separable perforation line 38 extends around outer sheath 36. Upon inflation of airbag 30, the pressure of airbag 30 forces perforation line 38 to separate thereby releasing airbag 30 to expand to the inflated condition.

As noted hereinabove, safety trocar assembly 10 is configured to avoid overpenetration of the abdominal wall. A sensor opening 40 is provided in a distal face 42 of elongate tubular member 24. A sensor lumen 44 extends proximally from sensor opening 40, through elongate tubular member 24, and terminates within housing 22. In order to manipulate housing 22 relative to an abdominal wall, housing 22 is provided with a pair of housing wings 46. Additionally, a source of inflation fluid 48 is provided on housing 22 to transmit, insufflation fluid through lumen 28 in elongate tubular member 24 in order to insufflate a body cavity to provide a working space for a surgical procedure.

In order to expand airbag 30 from the deflated to the inflated condition upon penetration of safety trocar assembly 10 through the abdominal wall, a trigger mechanism 50 is located on housing 22 and is provided to synchronize a change in condition sensed by a sensor associated with sensor opening 40 and sensor lumen 44, as described in more detail hereinbelow, with the inflation of airbag 30. Trigger mechanism 50 includes a trigger 52 which is provided to receive a signal from the sensor and operates to send inflation fluid through inflation lumen 34 and into airbag 30. A control knob 54 is provided to adjust the sensitivity of trigger 52.

Figures 5, 5A:
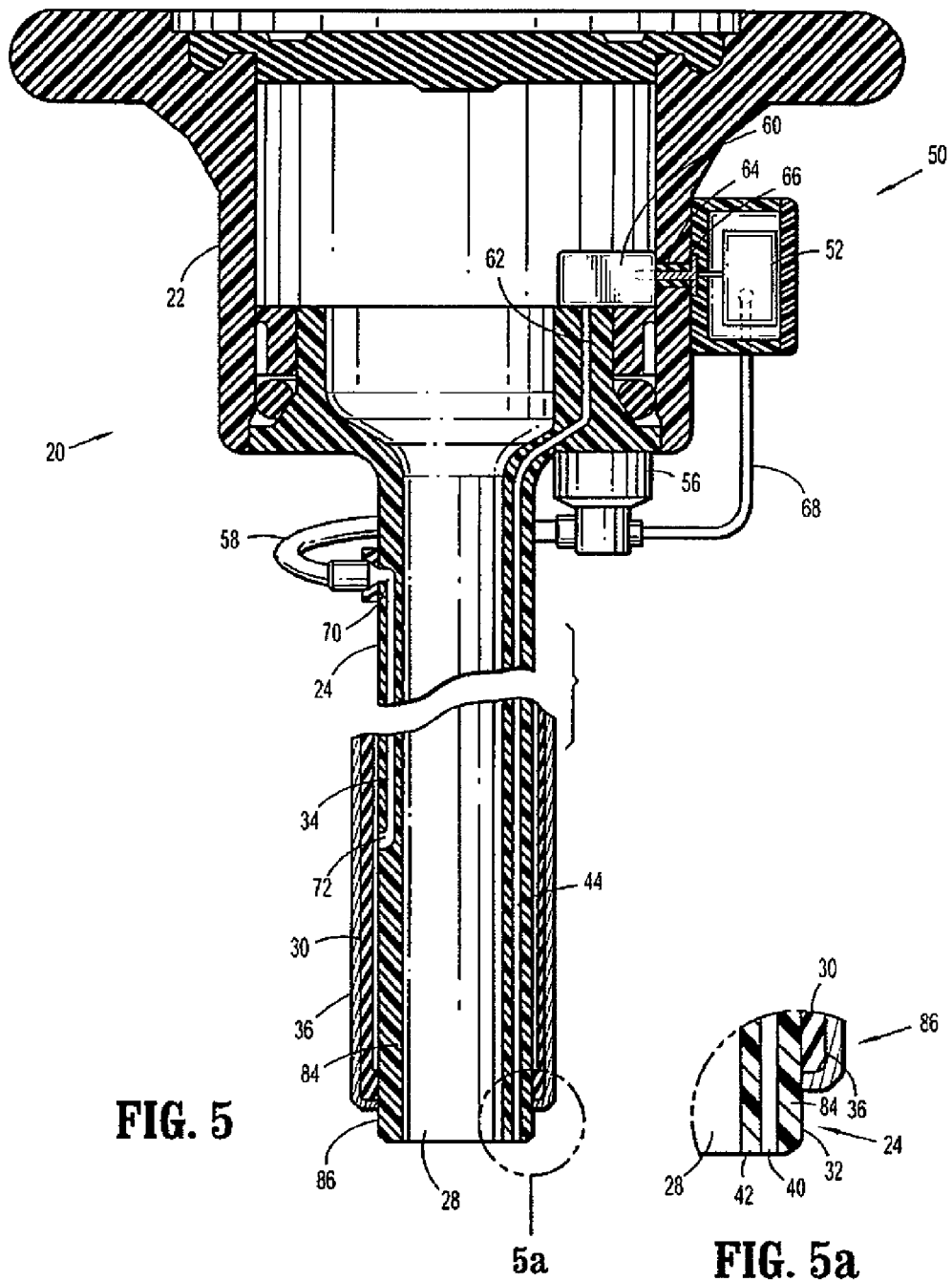
FIG. 5 is a cross-sectional view of the airbag cannula of FIG. 3 illustrating one embodiment of a sensor mechanism.
FIG. 5a is an enlarged area of detail view of FIG. 5.

With specific reference to FIGS. 2 and 5, trigger mechanism 50 includes a valve 56 which controls the flow of fluid into airbag 30. Valve 56 is connected to inflation lumen 34 by an inflation hose 58. In this embodiment, the particular sensor is an air pressure sensor 60 positioned within housing 22 and in fluid communication with a proximal end 62 of sensor lumen 44. Air pressure sensor 60 is provided to detect changes in air pressure within sensor lumen 44. Specifically, when distal face 42 of elongate tubular member 24 is positioned against tissue, air pressure sensor 60 pressurizes sensor lumen 44 with a predetermined amount of air pressure. Sensor opening 40, being positioned on distal face 42 of elongate tubular member 24, seals the distal end of sensor lumen 44 against the tissue in the manner described in more detail hereinbelow.

Trigger mechanism 50 may be formed as an integral part of housing 22 of cannula 20 or, as shown, may be formed as a detachable component. Air pressure sensor 60 includes a port 64 which is engageable with a connector 66 on trigger mechanism 50. Trigger 52 is connected to, and operates, valve 56 by a control hose 68. Thus, changes in air pressure detected by air pressure sensor 60 are communicated to trigger 52 which in turn operates to actuate valve 56.

Figure 4:
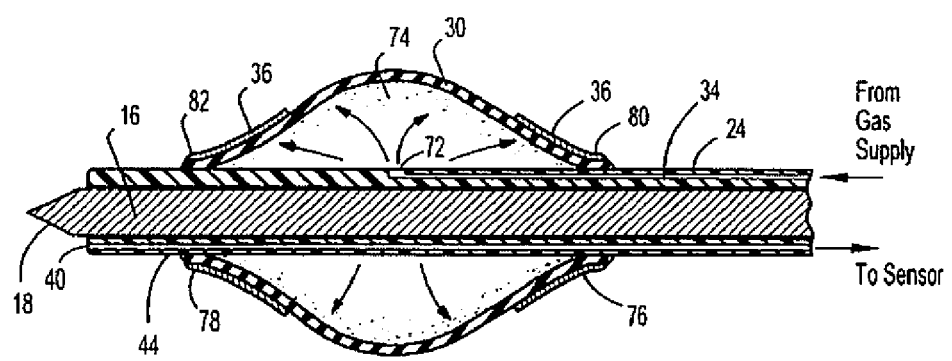
FIG. 4 is a side view, shown in section, taken along line 4-4 of FIG. 1.

Referring now to FIGS. 4 and 5, inflation hose 58 is connected to a proximal port 70 of inflation lumen 34 (FIG. 5) and a distal port 72 of inflation lumen 34 is in fluid communication with an interior 74 of airbag 30 (FIG. 4). As shown, passage of a fluid such as, for example, a gas, through inflation lumen 34 and out of distal port 72 moves airbag 30 from the deflated condition (FIG. 3) to the inflated condition as shown in FIG. 4.

With continued reference to FIG. 4, proximal and distal ends 76 and 78, respectively, of airbag 30 are secured to outer surface 32 of elongate tubular member 24 by gluing, welding, heat sealing or shrinking, etc. or other known methods of securing a flexible material to a substrate. Similarly, proximal and distal ends 80 and 82, respectively, of outer sheath 36 are secured to outer surface 32 of elongate tubular member 24.

Referring to FIG. 5, it should be noted that inflation lumen 34 is formed within the wall 84 of elongate tubular member 24. Similarly, with reference to FIG. 5a, sensor lumen 44 is also formed within wall 84 of elongate tubular member 24. Airbag 30 along with outer sheath 36 are located at a position proximal of distal end 86 of elongate tubular member 24. It should be further noted that, while sensor opening 40 is located at distal face 42 of elongate tubular member 24, sensor opening 40 may be provided at other locations on distal end 86 of elongate tubular member 24 such as, for example, a side of distal end 86 of elongate tubular member 24, etc. so long as sensor opening 40 is distal of airbag 30 and outer sheath 36.

Figures 6, 6A:
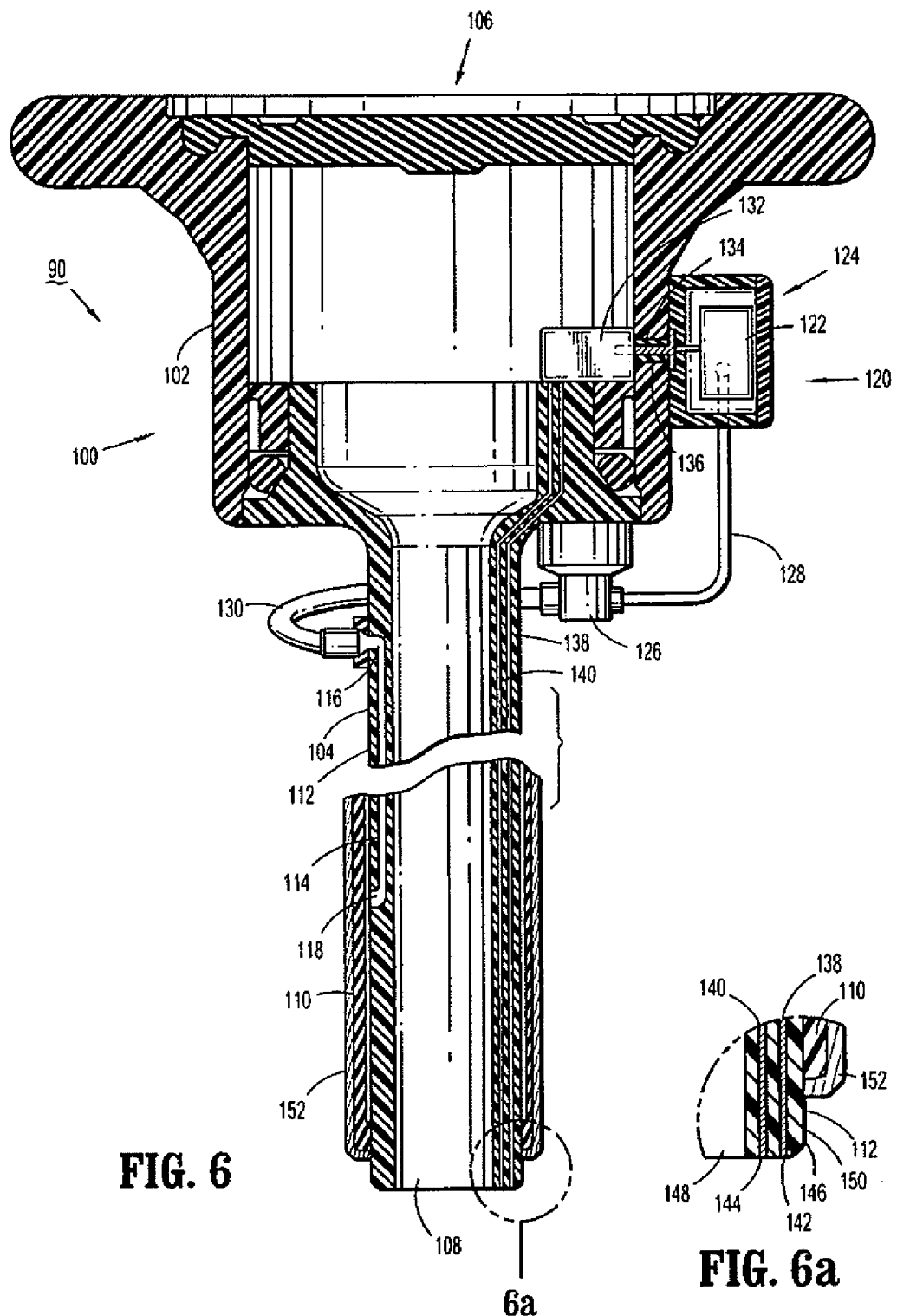
FIG. 6 is a cross-sectional view of the airbag cannula of FIG. 3 illustrating another embodiment of a sensor mechanism.
FIG. 6a is an enlarged area of detail view of FIG. 6.

Referring now to FIG. 6, there is disclosed an alternative embodiment of a safety trocar assembly 90. Safety trocar assembly 90 is similar to safety trocar assembly 10 described hereinabove and while not specifically shown here includes obturator 12. Safety trocar assembly 90 additionally includes an airbag cannula 100 having a housing 102 and an elongate tubular member 104 extending distally from housing 102. A throughbore 106 extends through housing 102 and a lumen 108 extends through elongate tubular member 104. An airbag 110 is provided on an outer surface 112 of elongate tubular member 104. Airbag 110 is substantially similar to airbag 30 described hereinabove. An inflation lumen 114 is formed within elongate tubular member 104 and includes a proximal port 116 and a distal end port 118 which is in fluid communication with airbag 110.

Similar to safety trocar assembly 10 described hereinabove, safety trocar assembly 90 includes a trigger mechanism 120 including a trigger 122 having an adjustable control knob 124. A valve 126 is included in trigger mechanism 120 and is connected to trigger 122 by a control hose 128. An inflation hose 130 extends between valve 126 and proximal port 116 to provide a source of inflation fluid to airbag 110.

Airbag cannula 110 includes an alternative sensing mechanism for detecting penetration of an abdominal wall. Specifically, an electrical sensor 132 is provided and includes a port 134 for engagement with a connector 136 of trigger mechanism 120. Electrical sensor 132 detects the change in resistance between that provided by the abdominal wall and the interior of the body cavity after safety trocar assembly 90 has penetrated the abdominal wall. First and second sensor wires 138 and 140, respectively, are provided in elongate tubular member 104. First and second sensor wires 138 and 140 may extend through a sensor lumen similar to sensor lumen 44 described hereinabove with respect to safety trocar assembly 10. In the presently disclosed embodiment, first and second sensor wires 138 and 140 are embedded within elongate tubular member 104. First and second sensor wires 138 and 140 terminate in first and second wire distal ends 142 and 144 which are spaced apart from one another. First and second sensor wires 138 and 140 extend through a distal end 146 of elongate tubular member 104 and are exposed through a distal face 148 of elongate tubular member 104.

Referring now to FIG. 6a, first and second sensor wires 138 and 140 are embedded in a side wall 150 of elongate tubular member 104. As distal ends 142 and 144 of first and second sensor wires 138 and 140 are placed in contact with the abdominal wall, sensor 132, and thus first and second sensor wires 138 and 140, is energized and detects a specific amount of resistance between distal ends 144 and 142. As distal end 146 of elongate tubular member 104 penetrates the abdominal wall and enters the body cavity, the resistance between distal ends 144 and 142 changes. This change in resistance is detected by sensor 132 which then signals trigger 124 to actuate valve 126 thereby inflating air bag 110. Similar to airbag cannula 20 described hereinabove, airbag cannula 100 includes an outer sheath 152 which surrounds airbag 110. Outer sheath 152 includes a separable perforation line (not shown) similar to perforation line 38 in outer sheath 36 described hereinabove.

Figures 7, 7A:
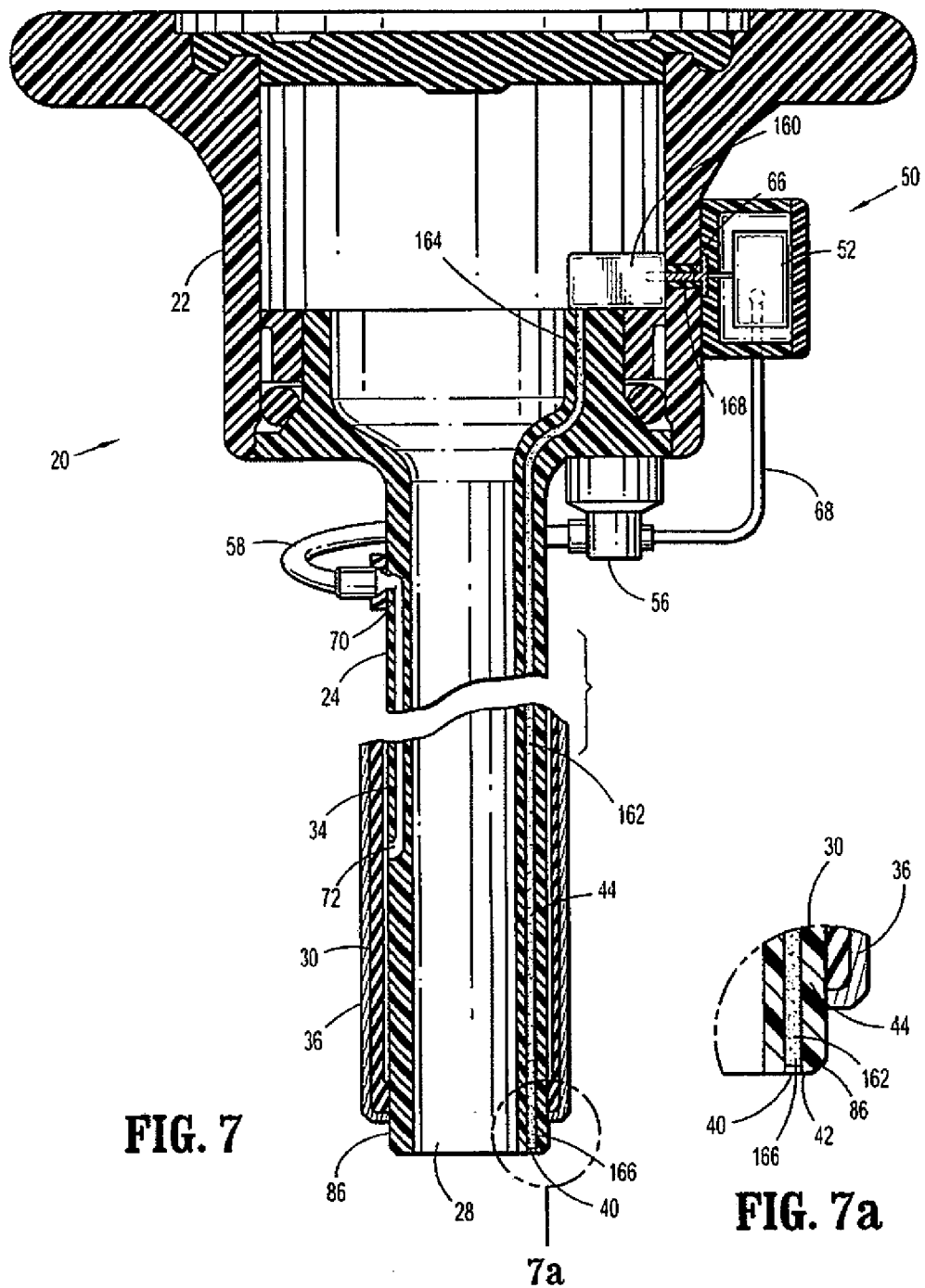
FIG. 7 is a cross-sectional view of the airbag cannula of FIG. 3 illustrating a further embodiment of a sensor mechanism.
FIG. 7a is an enlarged area of detail view of FIG. 7.

Referring now to FIGS. 7 and 7a, it will be appreciated that airbag cannula 20, described hereinabove, may be provided with a variety of other types of sensors in housing 22 and which extended through sensor lumen 44 to sensor opening 40. Examples of such sensors include ultrasound sensors, sonar sensors, etc. As shown in FIG. 7, airbag cannula 20 may be provided with an optical sensor 160 having a sensor fiber 162 extending distally from optical sensor 160 through sensor lumen 144. Sensor fiber 162 has a proximal end 164 connected to optical sensor 160 and a distal end 166 which is positioned within sensor opening 40 at distal end 86 of elongate tubular member 24. Sensor 160 includes a port 168 for receipt of connector 66 of trigger mechanism 50.

In use, when distal end 86 of elongate tubular member 24 is in engagement with an abdominal wall, distal end 166 of optical fiber 162 receives a first amount of light or a first image. After distal end 86 passes through the abdominal wall into the abdominal cavity, distal end 166 of optical fiber 162 detects a second amount of light or second image different from the first amount of light or first image. This difference is communicated through optical fiber 162 to optical sensor 160 which then signals trigger 52 to actuate valve 56 thereby inflating airbag 30. Thus, as distal end 86 of elongate tubular member 24 penetrates the abdominal wall, optical sensor 160 in combination with trigger mechanism 50 operate to instantaneously inflate airbag 30 thereby preventing any further advancement of elongate tubular member 24 through the abdominal wall. In this manner, underlying organs are protected from engagement with tissue penetrating tip 18 of obturator 12 and distal end 86 of airbag cannula 20.

Figure 8:
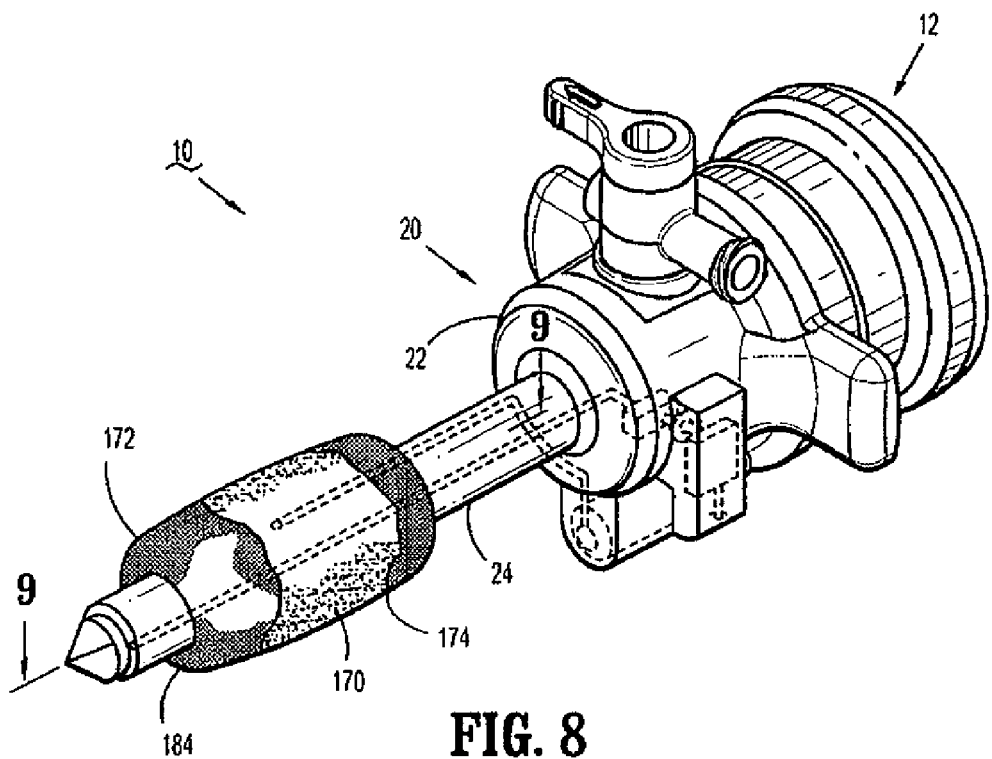
FIG. 8 is perspective view of an alternative embodiment of a safety trocar assembly incorporating an alternative embodiment of an airbag cannula.

Referring now to FIG. 8, safety trocar assembly 10 is disclosed with an alternative airbag 170. Safety trocar assembly 10 includes obturator 12 and airbag cannula 20 substantially as described hereinabove. As shown, airbag 170 forms a generally elongate doughnut shape around elongate tubular member 24. Similar to those embodiments described hereinabove an outer sheath 172 having a perforation line 174 surrounds airbag 170. In contrast to airbag 30 described hereinabove, distal and proximal ends 176 and 178 of airbag 170 are recurved inwardly and affixed to outer surface 32 of elongate tubular member 24 by welding, gluing, heat shrinking, etc. Likewise, distal and proximal ends 180 and 182 of outer sheath 172 are also recurved inwardly and secured against outer surface 32 of elongate tubular member 24.

Figure 9:
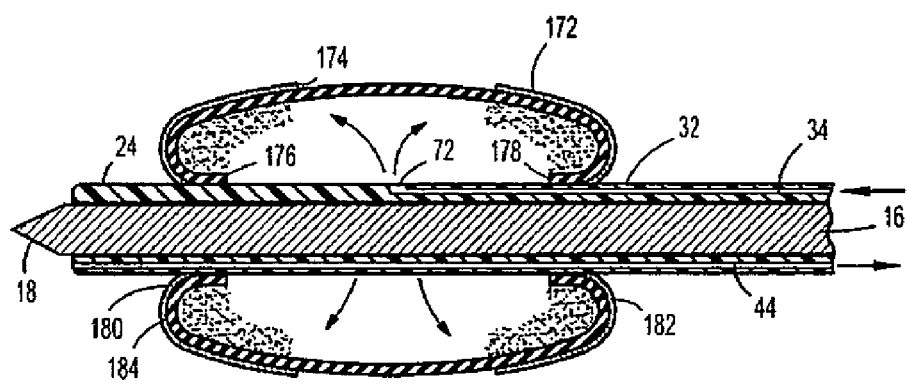
FIG. 9 is a cross-sectional view taken along line 9-9 of FIG. 8.

With specific reference to FIG. 9, upon inflation of airbag 170, a distal end surface 184 of airbag 170 projects distally beyond distal end 176 of airbag 170 to provided a "bumper" for engagement with the abdominal wall to thereby limit any further advancement of elongate tubular member 24 through the abdominal wall.

Figure 10:
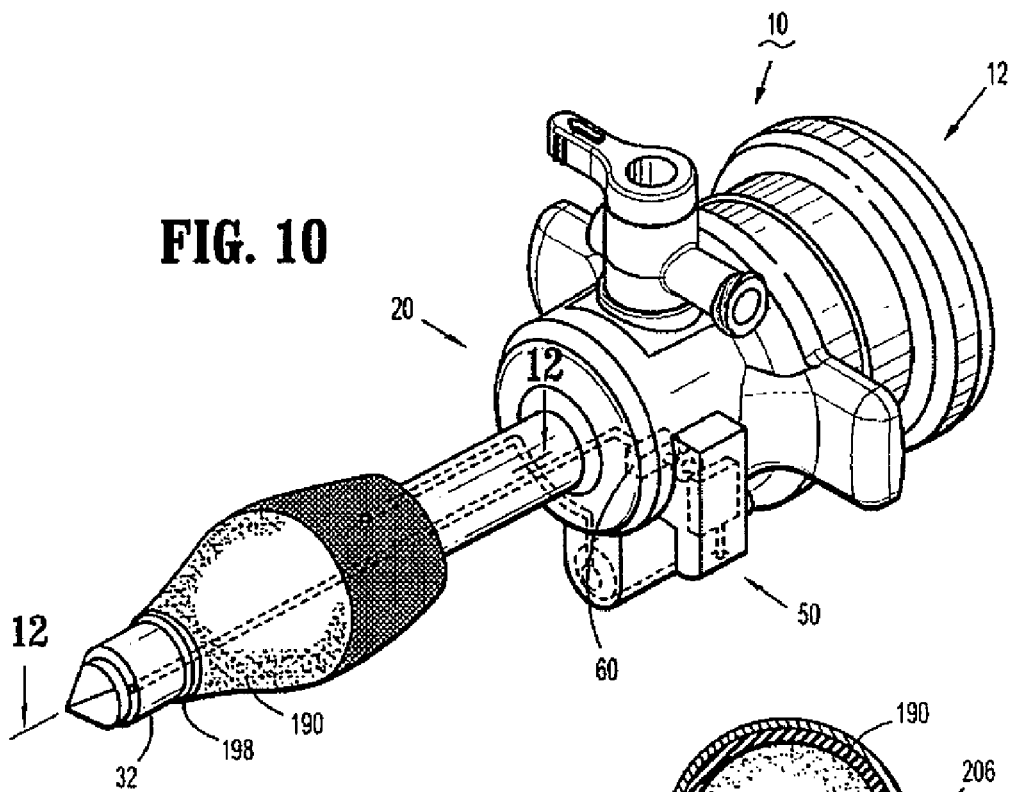
FIG. 10 is a perspective view of a further alternative embodiment of a safety trocar assembly incorporating a further alternative embodiment of an airbag cannula.
Figure 11:
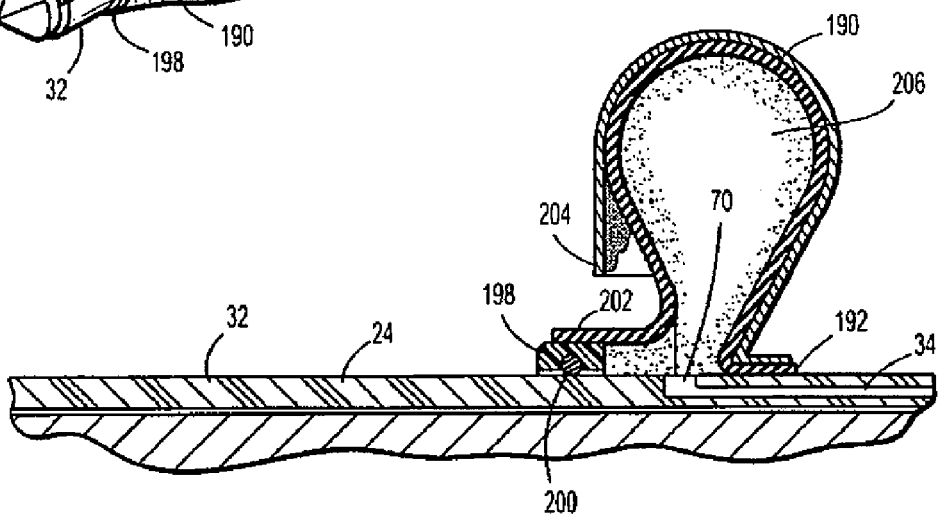
FIG. 11 is an enlarged cross-sectional view of the airbag of FIG. 10 in a first position.
Figure 12:
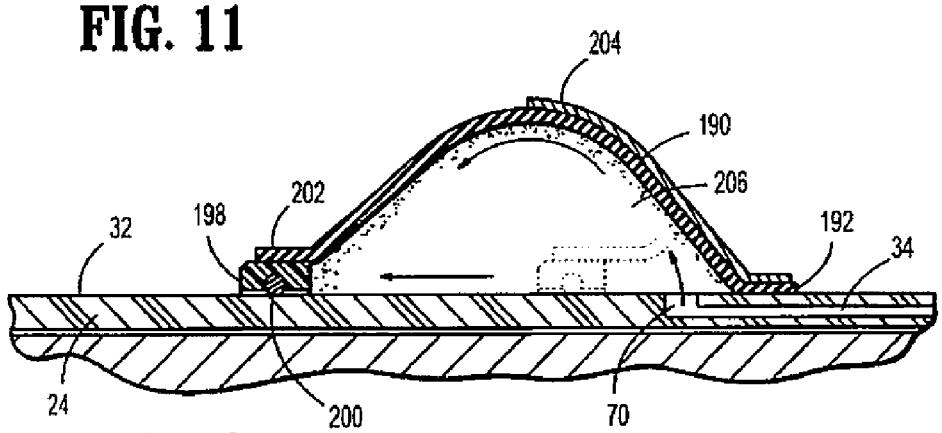
FIG. 12 is an enlarged cross-sectional view, taken along line 12-12 of FIG. 10, illustrating the airbag in a second position.

Referring now to FIGS. 10-12, and initially with regard to FIGS. 10 and 11, safety trocar assembly 10 is illustrated with a further alternative embodiment of an airbag 190. Safety trocar assembly 10 is substantially identical to that described hereinabove including obturator 12 and airbag cannula 20. Airbag cannula 20 includes housing 22 having elongate tubular member 24 extending distally therefrom. Trigger mechanism 50 along with sensor 60 are provided to inflate airbag 190 after elongate tubular member 24 penetrates abdominal wall.

Airbag 190 includes a proximal end 192 which is secured to outer surface 32 of elongate tubular member 24 in a manner described hereinabove. An outer sheath 194 surrounds airbag 190 in the undeployed position and includes a proximal end 196 which may be secured to outer surface 32 of elongate tubular member 24 or, alternatively, may be secured to proximal end 192 of airbag 190. In this embodiment, airbag 190 is configured to move distally along elongate tubular member 24 upon inflation to engage an abdominal wall. Specifically, a slide ring 198 is provided around elongate tubular member 24 and is longitudinally movable along elongate tubular member 24 from a proximal position wherein airbag 190 is in the deflated or undeployed condition to a distal position wherein airbag 190 is in the inflated condition. An O-ring 200 is provided between slide ring 198 and outer surface 32 of elongate tubular member 24 to seal airbag 190 against elongate tubular member 24. A distal end 202 of airbag 190 is secured to slide ring 198. A distal end 204 of outer sheath 194 may be temporarily secured to slide ring 198 and separates from slide ring 198 upon inflation of airbag 190.

Referring out of FIG. 12, upon forcing inflation fluid through inflation lumen 34 and out port 70 into an interior 206 of airbag 190, distal and 204 of outer sheath 194 separates from slide ring 198 and slide ring 198 moves distally along outer surface 32 of elongate tubular member 24 in response to the inflation of airbag 190. In this manner, advancement of elongate tubular member 204 through an abdominal wall proceeds until distal end 202 of airbag 190 engages the abdominal wall.

Figure 13:
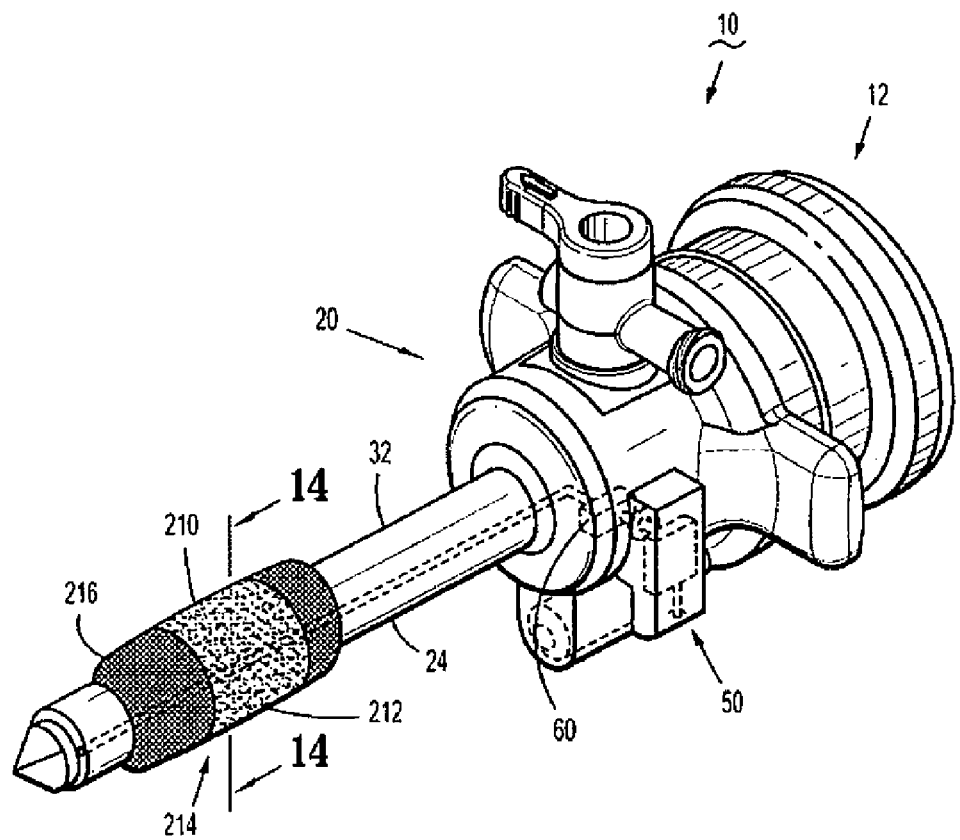
FIG. 13 is a perspective view of another alternative embodiment of a safety trocar assembly incorporating multiple airbags.
Figure 14:
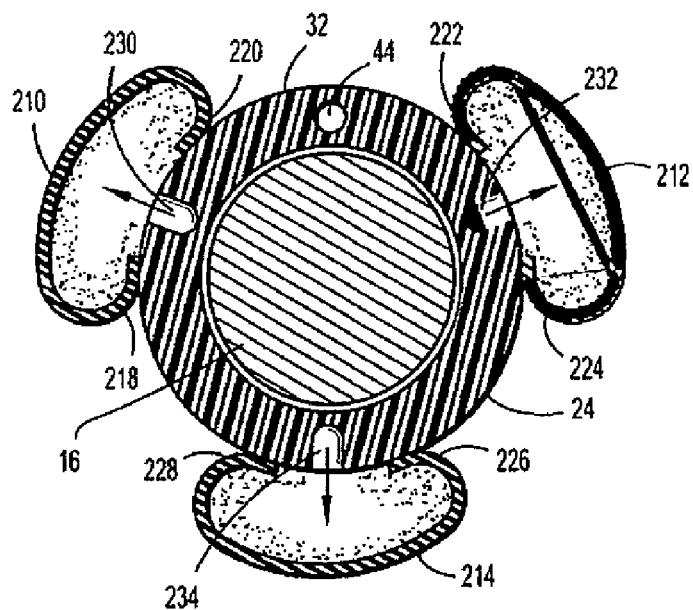
FIG. 14 is an enlarged cross-sectional view taken along line 14-14 of FIG. 13.

Referring now to FIGS. 13 and 14, and initially with regard to FIG. 13, safety trocar assembly 10 including obturator 12 and airbag cannula 20 is illustrated with multiple airbags 210, 212 and 214 located on outer surface 32 of elongate tubular member 24. An outer sheath 216 is provided to secure airbags 210, 212 and 214 against elongate tubular member 24 prior to inflation. As best shown in FIG. 14, recurved side edges 218 and 220 of airbag 210 are secured to outer surface 32 of elongate tubular member 24. Likewise, recurved side edges 222 and 224 and 226 and 228 of airbags 212 and 214 are similarly secured to outer surface 32 of elongate tubular member 24. Elongate tubular member 24 is formed with multiple inflation lumens terminating in inflation ports 230, 232 and 234 which are in fluid communication with airbags 210, 212 and 214 respectively. The provision of multiple airbags on safety trocar assembly 10 allows a surgeon to better view the incision in the abdominal wall as elongate tubular member 24 advances therethrough.

Figure 15:
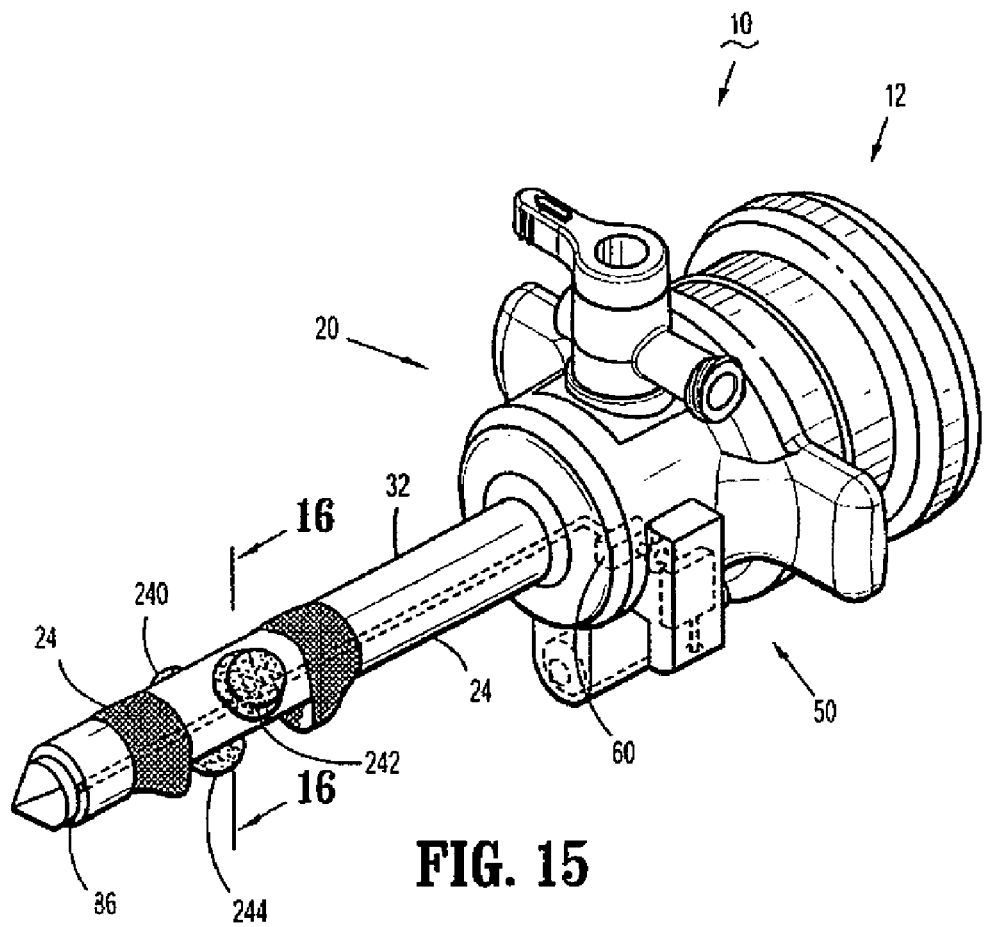
FIG. 15 is a perspective view of a further alternative embodiment of a safety trocar assembly incorporating a multiple airbag cannula.
Figure 16:
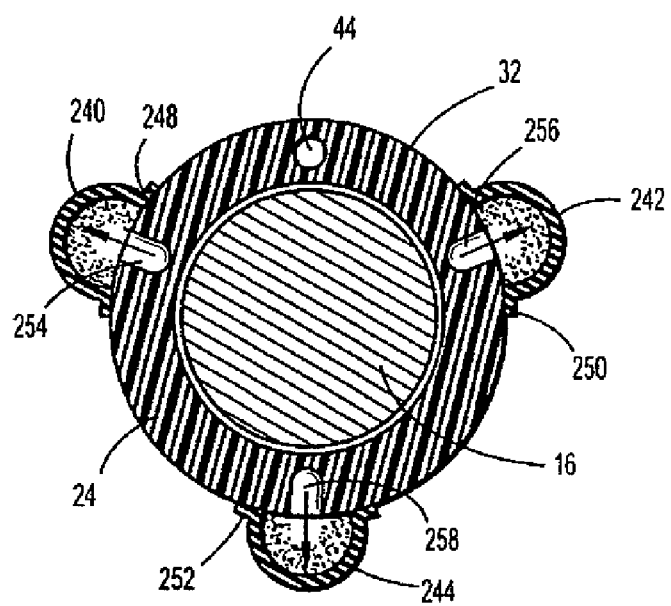
FIG. 16 is an enlarged cross-sectional view taken along line 16-16 of FIG. 15.

Referring now to FIGS. 15 and 16, and initially with regard to FIG. 15, safety trocar assembly 10 is substantially as described hereinabove including obturator 12 and airbag cannula 20. Like those embodiments described hereinabove, airbag cannula 20 includes air pressure sensor 60 and trigger mechanism 50 to cause inflation of the disclosed airbags upon penetration of an abdominal wall by distal end 86 of elongate tubular member 24. While the discussions herein are given in terms of distal end 86 of elongate tubular member 24 penetrating the abdominal wall, it will be appreciated that trocar assembly 10 as a whole is advanced against the abdominal wall such that tissue penetrating tip 18 of obturator 12 causes the penetration and informs the incision through the abdominal wall. Distal end 86 of airbag cannula 20 follows tissue penetrating tip 18 through the incision.

In this embodiment, as best shown in FIG. 16, a plurality of relatively small airbags such as, for example, airbag 240, airbag 242 and airbag 244 are formed about the circumference of elongate tubular member 24. Specifically, circumferential edges 248, 250 and 252 of airbags 240, 242 and 244, respectively, are fixed to outer surface 32 of elongate tubular member 24. Elongate tubular member 24 is provided with a plurality of longitudinally extending inflation lumens which terminate in inflation ports 254, 256 and 258 which are in fluid communication with airbags 240, 242 and 244 respectively. Similar to those embodiments described hereinabove, upon inflation of airbags 240, 242 and 244, outer sheath 246 separates to expose the airbags. Similar to the embodiments disclosed hereinabove, airbags 240, 242 and 244 are located proximal of distal end 86 of elongate tubular member 24.

Figure 17:
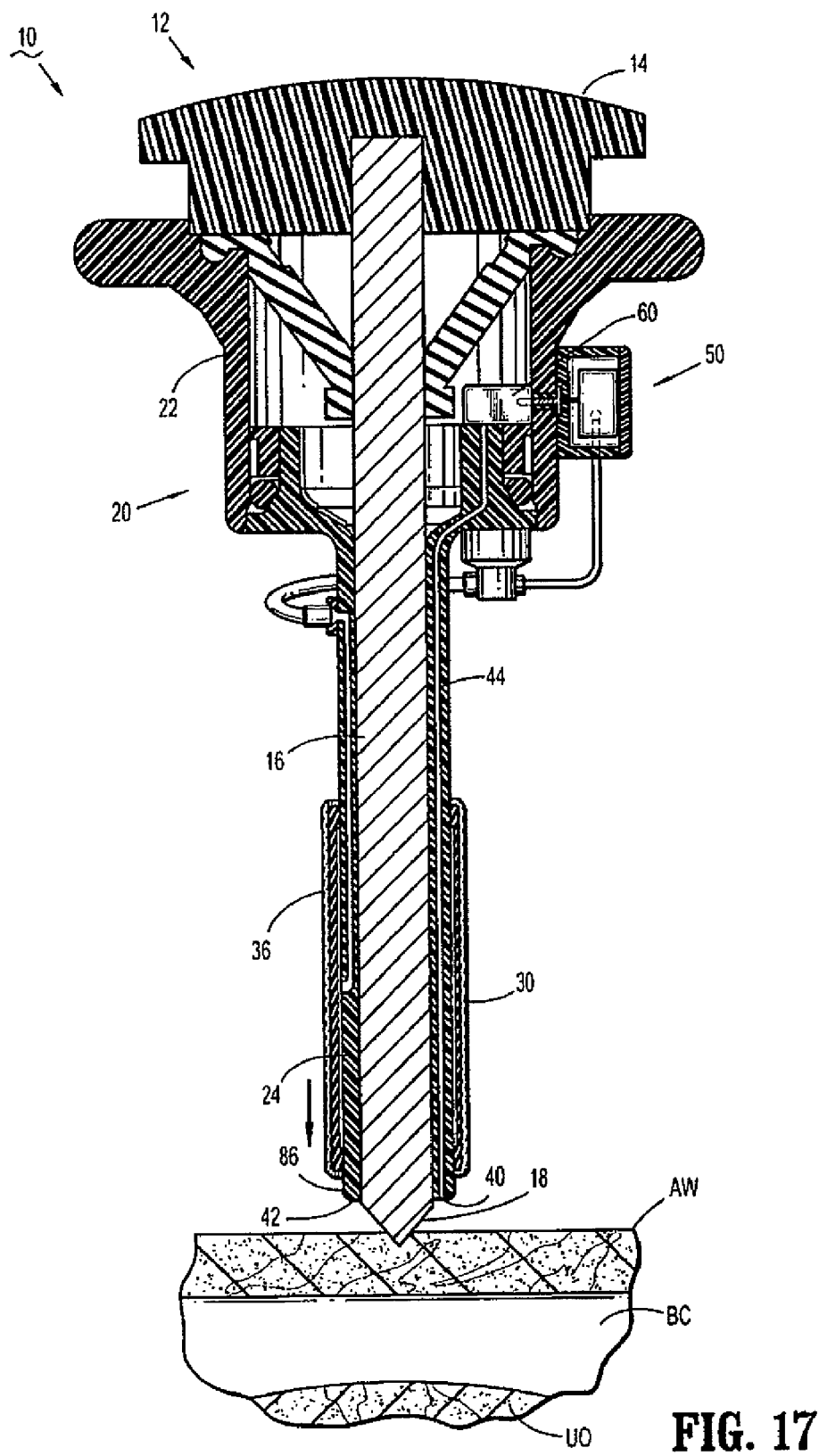
FIG. 17 is a side view, shown in section, of the safety trocar of FIG. 1 during initial penetration of an abdominal wall.
Figure 18:
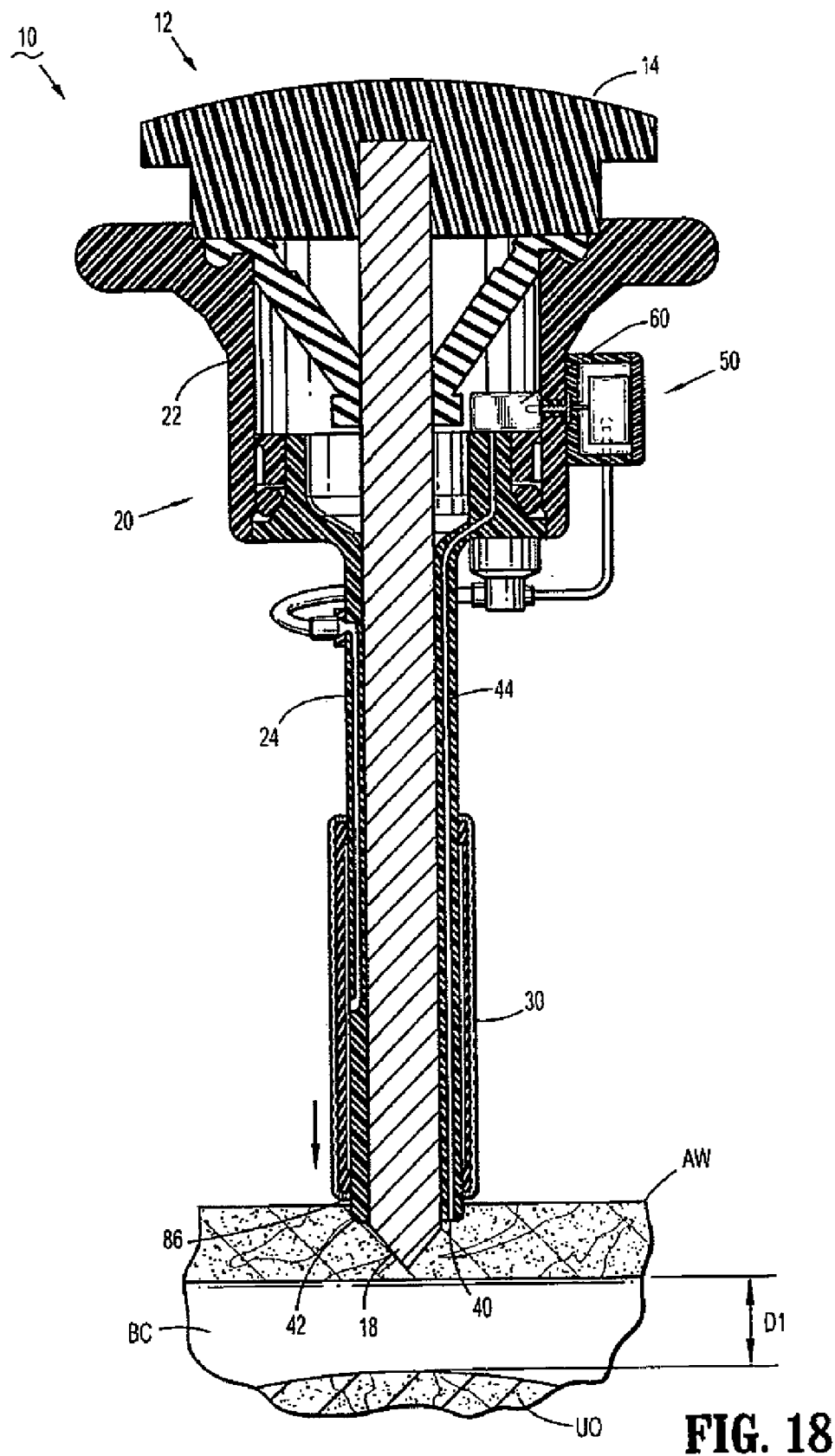
FIG. 18 is a side view, similar to FIG. 17, of the safety trocar assembly during penetration of the abdominal wall.
Figure 19:
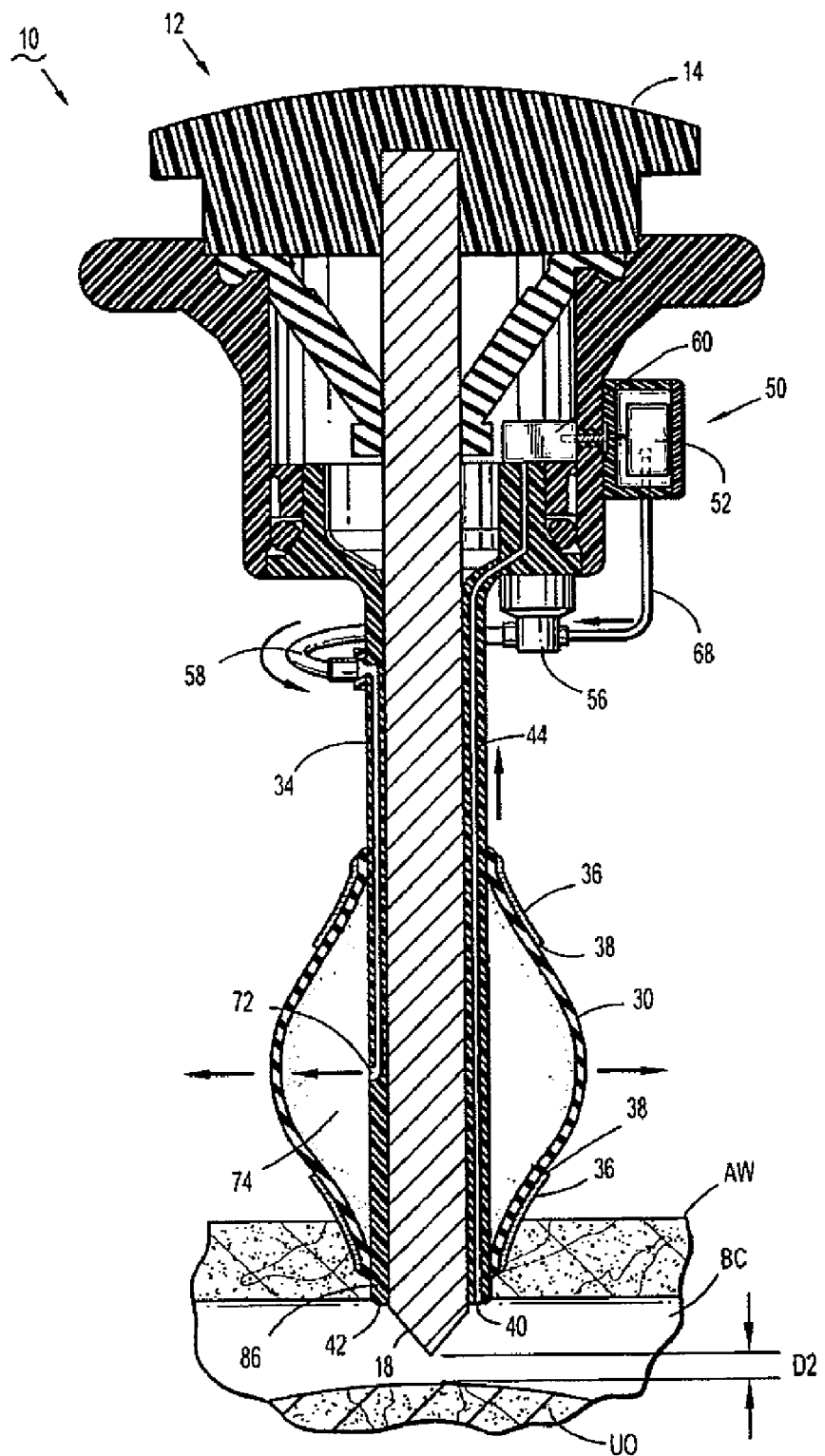
FIG. 19 is a side view, shown in section, of the safety trocar assembly after penetration of the abdominal wall.

Referring now to FIGS. 17-19, and initially with regard to FIG. 17, the use of safety trocar assembly 10, including airbag cannula 20, air pressure sensor 60 and airbag 30, to penetrate abdominal wall will now be described. Initially, obturator 12 is inserted through airbag cannula 20 is such that tissue penetrating tip 18 extends beyond distal end 86 of elongate tubular member 24. Airbag 30 is in a deflated condition and is restrained against elongate tubular member 24 by outer sheath 36. Safety trocar assembly 10 is advanced against an abdominal wall AW such that tissue penetrating tip 18 begins to penetrate or incise abdominal wall AW. As discussed hereinabove, safety trocar assembly 10 is provided to penetrate abdominal wall AW so as to position distal end 86 of airbag cannula 20 within a body cavity BC underlying abdominal wall AW without danger of damaging an underlying organ UO by tissue penetrating tip 18 of obturator 12 or distal end 86 of airbag cannula 20.

Referring now to FIG. 18, as tissue penetrating tip 18 of obturator 12 and distal end 86 of airbag cannula 20 are advanced into engagement with abdominal wall AW, sensor opening 40 is sealed against abdominal wall AW. Air pressure sensor 60 is activated to pressurize sensor lumen 44. Air pressure sensor 60 detects and maintains a predetermined amount of air pressure within sensor lumen 44. As shown, underlying organ UO is spaced a distance D1 from abdominal wall AW. Thus, it is necessary to insert tissue penetrating tip 18 a distance less than distance D1 into body cavity BC. This is accomplished by inflating airbag 30 upon penetration of abdominal wall AW by tissue penetrating tip 18 of obturator 12.

Referring to FIG. 19, as tissue penetrating tip 18 of obturator 12 and distal end 86 of airbag cannula 20 penetrate through abdominal wall AW and into body cavity BC, sensor opening 40 in distal face 42 of airbag cannula 20 is exposed or open to body cavity BC. Because body cavity BC has a pressure less than the pressure maintained in sensor lumen 44, the pressure in sensor lumen 44 drops. Sensor 60 detects the immediate change in pressure within sensor lumen 44 and signals trigger 52 of trigger mechanism 50. In response thereto, trigger 52 actuates valve 56 to cause inflation fluid to flow through inflation hose 58 and into inflation lumen 34. The inflation fluid passes through inflation port 72 into interior 74 of airbag 30 causing airbag 30 to rapidly expand. As airbag 30 expands, perforation line 38 of outer sheath 32 separates to release airbag 30 from the restrained condition.

The rapid expansion of airbag 30 which, as noted hereinabove, is positioned adjacent to distal end 86 of elongate tubular member 24 acts as a stop or bumper to prevent further advancement of elongate tubular member 24 and tissue penetrating tip 18 of obturator 12 into body cavity BC. Thus, tissue penetrating tip 18 of obturator 12 is restrained a distance D2 from underlying organ UO to prevent any damage to underlying organ UO.

It will be understood that various modifications may be made to the embodiments disclosed herein. For example, the disclosed airbags may be inflated manually by manually operating the valve of the trigger mechanism. Additionally, other forms of expandable members such as, for example, movable rigid stops, flexible wings, etc. may be provided and actuated by sensors to prevent overpenetration of an abdominal wall by tissue penetrating tip of an obturator. Further, other types of sensors may be provided to detect changes in conditions at the distal end of the cannula such as, for example, fluid pressure sensors, heat sensors, physical pressure sensors, mechanical devices such as movable rods within the sensor lumen etc. Additionally, the disclosed sensor detection mechanisms may be incorporated in other surgical instruments wherein proper positioning of distal ends of the surgical instruments may be detected by changes in conditions encountered by the distal ends of the surgical instruments. Still further, the disclosed airbag cannulas and sensors may be used in conjunction with known safety shields or penetrating tip retraction devices. Therefore, the above description should not be construed as limiting, but merely as exemplifications of particular embodiments. Those skilled in the art will envision other modifications within the scope and spirit of the claims appended hereto.

For example, while the various embodiments described and illustrated herein have the airbag 30 attached to an outer circumferential surface located near to the distal end of the cannula, it is also contemplated that the airbag may be located at any longitudinal position along the outer circumferential surface of the cannula. This position may reflect any one or more of various factors, such as the thickness of tissue to be penetrated, different internal distances D1, different types of tissue, and/or different thrust forces applied by the user. Still further, the length of the cannula may play a role in the appropriate position of the airbag 30 thereon.

Furthermore, while the various embodiments described and illustrated herein have the airbag 30 permanently attached to an outer circumferential surface of the cannula, it is also contemplated that the airbag may be selectively and/or adjustably attached to the outer circumferential surface of the cannula. In this manner, a user may adjust the position of the airbag 30 so as to accommodate different thickness of tissue (e.g., an obese patient may have a thicker tissue wall as compared to a thin patient), different internal distances D1 (e.g., a surgical procedure that involves insufflating an abdominal cavity may have an internal distance that is greater than a surgical procedure that does not involve insufflating the cavity), different types of tissue (e.g., a patient that has substantial scar tissue might require different penetrative forces as compared to a patient that has no such scarring) and/or different thrust forces applied by the user (e.g., a male surgeon may employ greater thrust forces as compared to a female surgeon).

The user of such a selectively and/or adjustably attachable airbag 30 might determine a position of the airbag prior to using the trocar and then leave the airbag 30 in that position for the duration of the surgical procedure. Alternatively a user might selectively adjust the position of the airbag 30 one or more times while actually using the trocar. For example, if a user selects a first position of the airbag 30 prior to a surgical procedure and then determines, after attempting to penetrate the abdominal wall AW, that the selected first position was too close to the distal end of the cannula (e.g., such that the airbag 30 prevents the tissue penetrating tip 18 from fully penetrating the tissue of the abdominal wall AW), the user may then select to adjust the position of the airbag 30 to a slightly more proximal position prior to continuing with the penetration of the abdominal wall AW. Still further, the user might elect to remove the airbag 30 entirely, at any point of the surgical procedure, if desired.

Still further, while the various embodiments described and illustrated herein have the airbag 30 attached to an outer circumferential surface of the cannula, it is also contemplated that the airbag may be attached to any component of the trocar. For example, the airbag 30 may be attached to the distal face of the housing 22. Of course, whatever component the airbag 30 is attached to, it is desirable that, when deployed, the airbag 30 is positioned so as to prevent over-penetration of the trocar through the abdominal wall AW and to avoid contact by the tissue penetrating tip 18 with the underlying tissues, e.g., internal organs.

The invention claimed is:

1. An airbag cannula comprising:
    a cannula having a housing and an elongate tubular member extending distally from the housing;
    an expandable member positioned on the elongate tubular member proximal of a distal end of the elongate tubular member, the expandable member movable from a collapsed position to an expanded position;
    a sensor disposed within the housing, the sensor having a sensor lumen extending therefrom, the sensor lumen formed through the elongate tubular member and having a sensor opening adjacent to the distal end of the elongate tubular member distal of the expandable member; and
    a trigger mechanism operatively associated with the sensor and the expandable member such that a change of condition sensed at the sensor opening operates to move the expandable member from the collapsed to the expanded position.

2. The airbag cannula as recited in claim 1, wherein the expandable member is an airbag positioned on the elongate tubular member, the elongate tubular member including an inflation lumen in fluid communication with the airbag, wherein the trigger mechanism includes a valve to inflate the airbag in response to a change in conditions detected by the sensor.

3. The airbag cannula as recited in claim 2, wherein the sensor is an air pressure sensor configured to detect changes in air pressure at the sensor opening.

4. The airbag cannula as recited in claim 2, wherein the sensor is an optical sensor including an optical fiber extending through the sensor lumen and terminating adjacent the sensor opening.

5. The airbag cannula as recited in claim 2, wherein the sensor is an ultrasound sensor.

6. The airbag cannula as recited in claim 2, wherein the sensor is a sonar sensor.

7. The airbag cannula as recited in claim 2, wherein a distal end of the airbag is longitudinally movable along and outer surface of the elongate tubular member.

8. The airbag cannula as recited in claim 2, wherein the airbag includes a plurality of circumferentially spaced airbags.

9. The airbag cannula as recited in claim 2, further comprising an outer sheath overlying the airbag to restrain the airbag in the collapsed position.

10. The airbag cannula as recited in claim 9, wherein the outer sheath includes a perforation line which is separable upon inflation of the airbag from the collapsed to the expanded position.

11. The airbag cannula as recited in claim 2, further comprising a source of fluid pressure operatively associated with the valve.

12. An airbag cannula comprising:
    a cannula having a housing and an elongate tubular member extending distally from the housing;
    an expandable member positioned on the elongate tubular member proximal of a distal end of the elongate tubular member, the expandable member movable from a collapsed position to an expanded position;
    an inflation lumen extending at least partially through the elongate tubular member and being disposed in fluid communication with the expandable member;
    a sensor disposed within the housing, the sensor having a sensor lumen extending therefrom, the sensor lumen formed through the elongate tubular member and having a sensor opening adjacent to the distal end of the elongate tubular member; and
    a trigger mechanism operatively associated with the sensor and the expandable member such that a change of condition sensed at the sensor opening operates to move the expandable member from the collapsed to the expanded position, the trigger mechanism being disposed in fluid communication with the inflation lumen.

13. The airbag cannula as recited in claim 12, wherein the trigger mechanism includes a valve in fluid communication with the inflation lumen, the valve adapted to provide fluid to the inflation lumen upon a change of condition sensed at the sensor opening.

14. The airbag cannula as recited in claim 13, wherein the trigger mechanism includes a trigger operatively associated with the sensor and the valve, the trigger adapted to actuate the valve upon a change in pressure detected by the sensor.

15. The airbag cannula as recited in claim 12, wherein the trigger mechanism is fluidly connected to the inflation lumen by a tube external to the elongate tubular member.

16. The airbag cannula as recited in claim 15, wherein the inflation lumen defines an opening on a exterior surface of the elongate tubular member for receiving the tube.

17. An airbag cannula comprising:
    a cannula having a housing and an elongate tubular member extending distally from the housing;
    an expandable member positioned on the elongate tubular member proximal of a distal end of the elongate tubular member, the expandable member movable from a collapsed position to an expanded position;
    a sensor disposed within the housing, the sensor having a sensor lumen extending therefrom, the sensor lumen formed through the elongate tubular member and having a sensor opening adjacent to the distal end of the elongate tubular member, the sensor opening being positionable against tissue; and a trigger mechanism operatively associated with the sensor and the expandable member such that a change of condition sensed by the sensor operates to move the expandable member from the collapsed to the expanded position.

18. The airbag cannula as recited in claim 17, wherein the sensor is an air pressure sensor configured to detect changes in air pressure at the sensor opening and within the sensor lumen.

19. The airbag cannula as recited in claim 17, wherein the sensor is adapted to pressurize the sensor lumen upon positioning of the sensor opening against tissue.

20. The airbag cannula as recited in claim 19, wherein the change of condition sensed by the sensor is the pressurization of the sensor lumen.

* * * * *